United States Patent
Cain et al.

(10) Patent No.: US 11,999,084 B2
(45) Date of Patent: Jun. 4, 2024

(54) ROTARY INJECTION MOLDING APPARATUS FOR PRODUCING PLASTIC COMPONENTS SUCH AS SYRINGES

(71) Applicant: BAYER HEALTHCARE LLC, Whippany, NJ (US)

(72) Inventors: Brian Cain, Elizabeth, PA (US); Matthew Schrauder, Mars, PA (US); Theodore B. Lemke, Saukville, WI (US); Randy J. Krell, West Bend, WI (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1060 days.

(21) Appl. No.: 16/334,463

(22) PCT Filed: Sep. 25, 2017

(86) PCT No.: PCT/US2017/053241
§ 371 (c)(1),
(2) Date: Mar. 19, 2019

(87) PCT Pub. No.: WO2018/063988
PCT Pub. Date: Apr. 5, 2018

(65) Prior Publication Data
US 2020/0094454 A1   Mar. 26, 2020

Related U.S. Application Data

(60) Provisional application No. 62/400,413, filed on Sep. 27, 2016.

(51) Int. Cl.
*A61M 5/31* (2006.01)
*A61M 5/178* (2006.01)
(Continued)

(52) U.S. Cl.
CPC ......... *B29C 45/0046* (2013.01); *A61M 5/178* (2013.01); *A61M 5/3129* (2013.01);
(Continued)

(58) Field of Classification Search
CPC .......... A61M 5/14546; A61M 5/14566; A61M 5/007
See application file for complete search history.

(56) References Cited

U.S. PATENT DOCUMENTS 3,256,892 A   6/1966   Esposito, Jr.
3,376,999 A   4/1968   Hart et al.
(Continued)

FOREIGN PATENT DOCUMENTS

JP   2006271665 A   * 10/2006
JP   2007098698 A   *  4/2007
(Continued)

OTHER PUBLICATIONS

May 13, 2016—PCT_IPRP_with_Written_Opinion_(dated May 12, 2015) for PCT Appln. No. PCT//US2014/063477.
(Continued)

*Primary Examiner* — William R Carpenter
(74) *Attorney, Agent, or Firm* — David Schramm; Joseph L. Kent; James R. Stevenson

(57) ABSTRACT

A syringe includes a barrel having a proximal end, a distal end, and a sidewall extending substantially circumferentially between the proximal end and the distal end along a longitudinal axis. The barrel is formed from an injection molding process including aligning a mold die defining an internal shape of the barrel in a molding cavity defining an external shape of the barrel, the molding cavity defined by first and second mold sections. Each mold section includes at least one gate adapted to control the flow of a molding material into the molding cavity. The gates of each mold section are
(Continued)

opened to permit the first and second melt streams of molding material to fill the molding cavity surrounding the mold die, where the molding material takes the shape of the molding cavity.

8 Claims, 13 Drawing Sheets

(51) Int. Cl.
A61M 5/315 (2006.01)
B29C 45/00 (2006.01)
B29C 45/06 (2006.01)
B29C 45/16 (2006.01)
B29C 45/26 (2006.01)
B29L 31/00 (2006.01)

(52) U.S. Cl.
CPC ..... *A61M 5/31515* (2013.01); *B29C 45/0025* (2013.01); *B29C 45/062* (2013.01); *B29C 45/1618* (2013.01); *B29C 45/164* (2013.01); *B29C 45/261* (2013.01); *A61M 2207/00* (2013.01); *A61M 2207/10* (2013.01); *B29C 2045/0027* (2013.01); *B29L 2031/7544* (2013.01)

(56) References Cited

U.S. PATENT DOCUMENTS

| | | | |
|---|---|---|---|
| 3,855,380 A * | 12/1974 | Gordon | B29D 23/20 264/161 |
| 3,923,943 A | 12/1975 | Iriko et al. | |
| 4,039,641 A | 8/1977 | Collins | |
| 4,244,409 A | 1/1981 | Wilson et al. | |
| 4,342,184 A | 8/1982 | Van Eck et al. | |
| 4,411,656 A | 10/1983 | Cornett, III | |
| 4,681,606 A | 7/1987 | Swan, Jr. et al. | |
| 4,790,822 A | 12/1988 | Haining | |
| 5,007,904 A * | 4/1991 | Densmore | A61M 5/14546 604/218 |
| 5,047,017 A | 9/1991 | Koska | |
| 5,061,252 A | 10/1991 | Dragosits | |
| 5,122,327 A | 6/1992 | Spina et al. | |
| 5,242,422 A | 9/1993 | Schneberger et al. | |
| 5,330,425 A | 7/1994 | Utterberg | |
| 5,383,858 A | 1/1995 | Reilly et al. | |
| 5,873,861 A | 2/1999 | Hitchins et al. | |
| 5,900,205 A | 5/1999 | Sadr et al. | |
| 5,947,935 A * | 9/1999 | Rhinehart | A61M 5/14546 604/218 |
| 6,017,330 A | 1/2000 | Hitchins et al. | |
| 6,041,775 A | 3/2000 | Century | |
| 6,224,577 B1 | 5/2001 | Dedola et al. | |
| 6,322,535 B1 | 11/2001 | Hitchins et al. | |
| 6,394,983 B1 | 5/2002 | Mayoral et al. | |
| 6,652,489 B2 | 11/2003 | Trocki et al. | |
| 6,665,489 B2 | 12/2003 | Collart | |
| 6,673,303 B2 | 1/2004 | White et al. | |
| 6,702,978 B1 | 3/2004 | Kuehn | |
| 6,719,733 B1 | 4/2004 | Heffernan et al. | |
| 6,790,027 B1 | 9/2004 | Callen et al. | |
| 6,984,222 B1 | 1/2006 | Hitchins et al. | |
| 7,175,609 B1 | 2/2007 | Gray | |
| 7,740,792 B2 | 6/2010 | Haury et al. | |
| 8,414,540 B2 * | 4/2013 | Schriver | A61M 5/14546 604/154 |
| 9,173,995 B1 | 11/2015 | Tucker et al. | |
| 9,199,033 B1 | 12/2015 | Cowan et al. | |
| 2002/0048642 A1 | 4/2002 | Beck | |
| 2002/0055719 A1 | 5/2002 | Lo | |
| 2002/0128606 A1 * | 9/2002 | Cowan | G01D 5/12 604/181 |
| 2003/0121927 A1 | 7/2003 | Rice et al. | |
| 2004/0262818 A1 | 12/2004 | Takeuchi | |
| 2005/0148720 A1 | 7/2005 | Li et al. | |
| 2005/0161866 A1 | 7/2005 | Batlaw et al. | |
| 2006/0029720 A1 | 2/2006 | Panos et al. | |
| 2008/0157444 A1 | 7/2008 | Melsheimer | |
| 2008/0200916 A1 | 8/2008 | Murphy et al. | |
| 2010/0241085 A1 | 9/2010 | Haury et al. | |
| 2012/0031870 A1 | 2/2012 | Porter et al. | |
| 2013/0281940 A1 | 10/2013 | Gelblum et al. | |
| 2016/0199591 A1 * | 7/2016 | Matsui | B29C 45/261 425/129.1 |
| 2016/0271330 A1 | 9/2016 | Rhinehart et al. | |

FOREIGN PATENT DOCUMENTS

| | | | | |
|---|---|---|---|---|
| JP | 2007223217 A | * | 9/2007 | |
| WO | 2008090424 A1 | | 7/2008 | |
| WO | 2012015897 A1 | | 2/2012 | |
| WO | 2012139551 A2 | | 10/2012 | |
| WO | WO-2012150897 A1 | * | 11/2012 | ............ A61M 5/34 |
| WO | 2013099447 A1 | | 7/2013 | |
| WO | 2015121320 A1 | | 8/2015 | |

OTHER PUBLICATIONS

Admer, Mitsui Chemicals America, Inc. of Rye Brook, New York, (www.mitsuichemicals.com/cha.htm), Retrieved from the Internet Sep. 11, 2007.
"International Preliminary Report on Patentability from PCT Application No. PCT/US2017/053241", dated Apr. 11, 2019.
Lamonte, R.R. and D. McNally, Cyclic Olefin Copolymers, Advanced Materials & Processes, (Mar. 2001), 4 pages.
Whitmore, E.M., "Standards & Practices of Plastics Molders—Guidelines for Molders and Their Customers, Molders Division," Sponsored by the Society of the Plastics Industry, Inc. (1993).
Zeonor 1410R, Zeon Chemicals LP of Louisville, Kentucky, Material Safety Data Sheet, Oct. 18, 2002.

* cited by examiner

ROTARY INJECTION MOLDING APPARATUS FOR PRODUCING PLASTIC COMPONENTS SUCH AS SYRINGES

CROSS REFERENCE TO RELATED APPLICATIONS

This application is a 371 national phase application of PCT International Application No. PCT/US2017/053241, filed on Sep. 25, 2017, and claims the priority to U.S. Provisional Patent Application No. 62/400,413, filed on Sep. 27, 2016, the disclosures of which are incorporated herein by reference in their entirety.

BACKGROUND OF THE DISCLOSURE

Field of the Disclosure

This disclosure relates broadly to rotary injection molding of plastic components and, more particularly, pertains to an apparatus and method for producing plastic components, such as a syringe, in multi-shot injection molding by injecting resin from multiple melt streams of a same or different material into a mold. Also disclosed is a plastic part produced using the rotary injection molding apparatus and method.

Description of Related Art

Plastic parts may be produced using a variety of molding and/or injection processes. In general, an injection cycle for producing a plastic part includes injecting molten plastic into a multi-section mold where the molten plastic takes the shape of a mold cavity and cools to form a solid part. The solid part is then released or ejected from the mold cavity, typically by separating the sections of the mold to allow the solid part to be removed manually or by mechanical means.

Several known devices and processes may be employed to inject the molten plastic into the mold cavity. One type of molding device or apparatus uses runners, which are passageways in the mold leading from the mold cavity to an external injector nozzle. Molten plastic is delivered from the injector nozzle and travels through the runners into the mold cavity where the molten plastic solidifies. Heat may be applied to the mold along the runners to facilitate the flow of the molten plastic into the mold cavity. In this case, the runners are referred to as hot runners, whereas runners to which heat is not applied are referred to as cold runners.

A disadvantage of molding devices or apparatuses having runners is that the molten plastic remains and solidifies in the runners at the end of each injection cycle. As such, the solidified plastic must be ejected with the formed plastic part in preparation for subsequent injection cycles. This results in wasted material that must be removed from the plastic part prior to use of the plastic part. An additional disadvantage of runners is that the material properties of the plastic part may be compromised at the injection point where the runner meets the mold cavity, due to inconsistent solidification of the molten plastic. The injection point may, for example, exhibit discoloration, reduced strength, and increased brittleness in comparison to the remainder of the plastic part.

An alternative to using cold or hot runners is direct gating, in which an injection gate opens directly into the mold cavity. As runners are not necessary in direct gating, many of the deficiencies of molds having runners are reduced or eliminated. However, in direct gating, the injection gate must be in direct proximity to mold cavity, which may require the injection gate to be connected to the mold. As a result, the gates must be capable of moving with the mold when the section of the mold are separated to release the plastic part at the end of each injection cycle. Additionally, space constraints of the molding device or apparatus may limit the possible locations for the injection gate.

An example of a known process for producing a plastic part is two-shot or multi-shot molding, in which multiple shots of resin are injected into a cavity or cavities of a mold. In conventional two-shot or multi-shot molding, the entire mold or portions of the mold are rotatably mounted to the molding machine so that molded parts may be transferred between an injection station, where the resin is inserted into the mold, and an ejection station, where the completed part is removed from the mold. When the entire mold rotates, this is commonly referred to as the rotary platen technique. This rotation is achieved by a hydraulic cylinder or electric motor, which provides the means of movement for part transfer. This rotation typically requires 180° of rotation with other increments possible for additional shots or functions. This rotation is integrated with the movable platen of the machine and cooperates with a fixed metal mold mounted on the stationary platen.

Conventionally, to produce a two-shot plastic part, one shot of material is first injected into the mold, the mold then opens and the platen rotates the mold 180°, and the mold closes again. A second shot, typically of another material different that the first shot, is then injected around the first shot to create a plastic part with two colors or materials. When the mold opens this time, the completed part may be ejected by a mechanical ejection means. The mold will then rotate and close to repeat the cycle again. The rotary platen technique is frequently used because it permits parallel simultaneous injection of both shots, albeit in different mold cavities.

An example of a multi-shot injection mold which produces a plastic part from multiple melt streams known in the art is U.S. Pat. No. 6,790,027 to MGS Mfg. Group, Inc. U.S. Pat. No. 6,790,027 discloses a multi-shot injection mold in which resin from multiple melt streams is sequentially injected into successive mold cavities to form an overmolded plastic part. However, the use of multiple mold cavities consequently necessitates the use of multiple injection steps.

In view of the existing art, there exists a need for an improved rotary injection molding apparatus, method, and plastic parts produced therefrom.

SUMMARY OF THE DISCLOSURE

In some examples, a syringe includes a barrel having a proximal end, a distal end, and a sidewall extending substantially circumferentially between the proximal end and the distal end along a longitudinal axis. The barrel is formed from an injection molding process including aligning a mold die defining an internal shape of the barrel in a molding cavity defining an external shape of the barrel, the molding cavity defined by a first mold section and a second mold section. Each mold section includes at least one gate adapted to control the flow of a molding material into the molding cavity. The at least one gate of the first mold section is located diametrically opposite the at least one gate of the second mold section within the molding cavity. A first melt stream of molding material is supplied to the gate of a first mold section, and a second melt stream of molding material is supplied to the gate of the second mold section. The gates of the first mold section and the second mold section are opened to permit molding material from the first melt stream and the second melt stream to fill the molding cavity surrounding the mold die, where the molding material takes the shape of the molding cavity.

In some examples, the syringe further includes at least two parting lines formed on the barrel substantially parallel to the longitudinal axis, the at least two parting lines corresponding to an interface of the first mold section and the second mold section.

In some examples, the syringe further includes one or more gate marks formed on the barrel at the location of each of the gates of the first mold section and the second mold section.

In some examples, the one or more gate marks are located on the barrel substantially perpendicular to the at least two parting lines about the longitudinal axis.

In some examples, the syringe further includes a plunger inserted in the barrel and comprising at least two legs configured to engage a piston element of a fluid injector. The plunger is inserted in the barrel such that the at least two parting lines are aligned to bisect the at least two legs, thereby providing a visual indication of the orientation of the at least two legs.

In some examples, at least one of the first mold section and the second mold section includes one or more vacuum ports.

In some examples, at least one of the first mold section and the second mold section includes a groove configured to receive a vacuum venting seal.

In some examples, the injection molding process is performed using a rotary injection molding apparatus.

In some examples, the rotary injection molding apparatus includes a stationary first side plate including a plurality of alignment pins protruding from the first side plate and a second side plate slidably attached to the first side plate. The second side plate includes a plurality of alignment bores engageable with the plurality of alignment pins. An injection station includes the first mold section disposed on the first side plate and the second mold section disposed on the second side plate. The first mold section and the second mold section define the molding cavity. The first mold section includes a first gate adapted to inject a first molding material into the molding cavity from a first melt stream, and the second mold section includes a second gate adapted to inject a second molding material into the molding cavity from a second melt stream. An indexing plate assembly is rotatably attached to the second side plate, the indexing plate assembly including a plurality of mold dies, each mold die operatively alignable with the molding cavity via rotation of the indexing plate assembly.

In some examples, the rotary injection molding apparatus further includes a cooling station defining a cooling chamber operatively alignable with each mold die of the indexing plate assembly via rotation of the indexing plate assembly. The cooling chamber includes at least one fluid port adapted for circulating a cooling fluid into the cooling chamber.

In other examples, the present disclosure relates to a rotary injection molding apparatus for producing a plastic part. The rotary injection molding apparatus includes a stationary first side plate including a plurality of alignment pins protruding from the first side plate, and a second side plate slidably attached to the first side plate. The second side plate includes a plurality of alignment bores engageable with the plurality of alignment pins. An injection station includes a first mold section disposed on the first side plate and a second mold section disposed on the second side plate. The first mold section and the second mold section define one or more molding cavities. The first mold section includes a first gate adapted to inject a first molding material into each molding cavity from a first melt stream, and the second mold section includes a second gate adapted to inject a second molding material into each molding cavity from a second melt stream. An indexing plate assembly rotatably attached to the second side plate includes a plurality of mold dies, each mold die operatively alignable with the molding cavity via rotation of the indexing plate assembly.

In some examples, the rotary injection molding apparatus further includes a cooling station defining a cooling chamber operatively alignable with each mold die of the indexing plate assembly via rotation of the indexing plate assembly.

In some examples, the cooling chamber includes at least one fluid port adapted for circulating a cooling fluid into the cooling chamber.

In some examples, the rotary injection molding apparatus further includes an ejector station including an ejector cradle slidably connected to the second side plate, the ejector cradle adapted to disengage a completed plastic part from a corresponding mold die.

In some examples, at least one of the first mold section and the second mold section includes one or more vacuum ports, and at least one of the first mold section and the second mold section includes a groove configured to receive a vacuum venting seal.

The present disclosure also relates to a method of producing a plastic part via injection molding in a rotary injection molding apparatus. In some examples, the method includes aligning a mold die in a molding cavity, the molding cavity defined by a first mold section and a second mold section, each mold section including a gate adapted to control the flow of a molding material into the molding cavity, the gate of the first mold section located diametrically opposite the gate of the second mold section within the molding cavity. A first melt stream of molding material is supplied to the gate of the first mold section, and a second melt stream of molding material is supplied to the gate of the second mold section. The gates of the first mold section and the second mold section are opened to permit molding material from the first melt stream and the second melt stream to fill the molding cavity surrounding the mold die, where the molding material takes the shape of the molding cavity forming a plastic part.

In some examples, the method further includes realigning the mold die in a cooling chamber, where a cooling fluid is circulated about the cooling chamber to cool the plastic part.

In some examples, the method further includes realigning the mold die in an ejector station, where the plastic part is removed from the mold die.

In some examples, the first molding material includes the same material as the second molding material.

In some examples, the first molding material includes a different material than the second molding material.

In accordance with other examples, the disclosure of the present application may be characterized by one or more of the following clauses:

Clause 1. A syringe comprising:
a barrel having a proximal end, a distal end, and a sidewall extending substantially circumferentially between the proximal end and the distal end along a longitudinal axis, wherein the barrel is formed from an injection molding process comprising:
aligning a mold die defining an internal shape of the barrel in a molding cavity defining an external shape of the barrel, the molding cavity defined by a first mold section and a second mold section, each mold section comprising at least one gate adapted to control the flow of a molding material into the molding cavity, the at least one gate of the first mold section located diametrically opposite the at least one gate of the second mold section within the molding cavity;

supplying a first melt stream of molding material to the gate of a first mold section, and supplying a second melt stream of molding material to the gate of the second mold section; and opening the gates of the first mold section and the second mold section to permit molding material from the first melt stream and the second melt stream to fill the molding cavity surrounding the mold die, wherein the molding material takes the shape of the molding cavity.

Clause 2. The syringe of clause 1, further comprising at least two parting lines formed on the barrel substantially parallel to the longitudinal axis, the at least two parting lines corresponding to an interface of the first mold section and the second mold section.

Clause 3. The syringe of clauses 1 or 2, further comprising one or more gate marks formed on the barrel at the location of each of the gates of the first mold section and the second mold section.

Clause 4. The syringe of any of clauses 1 to 3, wherein the one or more gate marks are located on the barrel substantially perpendicular to the at least two parting lines about the longitudinal axis.

Clause 5. The syringe of any of clauses 1 to 4, further comprising a plunger inserted in the barrel and comprising at least two legs configured to engage a piston element of a fluid injector, and wherein the plunger is inserted into the barrel such that the at least two parting lines are aligned to bisect the at least two legs to provide a visual indication of the orientation of the at least two legs.

Clause 6. The syringe of any of clauses 1 to 5, wherein at least one of the first mold section and the second mold section comprises one or more vacuum ports.

Clause 7. The syringe of any of clauses 1 to 6, wherein at least one of the first mold section and the second mold section comprises a groove configured to receive a vacuum venting seal.

Clause 8. The syringe of any of clauses 1 to 7, wherein the injection molding process is performed using a rotary injection molding apparatus.

Clause 9. The syringe of any of clauses 1 to 8, wherein the rotary injection molding apparatus comprises:

a stationary first side plate comprising a plurality of alignment pins protruding from the first side plate;

a second side plate slidably attached to the first side plate, the second side plate comprising a plurality of alignment bores engageable with the plurality of alignment pins;

an injection station comprising a first mold section disposed on the first side plate and a second mold section disposed on the second side plate, the first mold section and the second mold section defining the molding cavity, the first mold section comprising a first gate adapted to inject a first molding material into the molding cavity from a first melt stream, and the second mold section comprising a second gate adapted to inject a second molding material into the molding cavity from a second melt stream; and an indexing plate assembly rotatably attached to the second side plate, the indexing plate assembly comprising a plurality of mold dies, each mold die operatively alignable with the molding cavity via rotation of the indexing plate assembly.

Clause 10. The syringe of any of clauses 1 to 9, wherein the rotary injection molding apparatus further comprises:

a cooling station defining a cooling chamber operatively alignable with each mold die of the indexing plate assembly via rotation of the indexing plate assembly, wherein the cooling chamber comprises at least one fluid port adapted for circulating a cooling fluid into the cooling chamber.

Clause 11. A rotary injection molding apparatus for producing a plastic part comprising:

a stationary first side plate comprising a plurality of alignment pins protruding from the first side plate;

a second side plate slidably attached to the first side plate, the second side plate comprising a plurality of alignment bores engageable with the plurality of alignment pins;

an injection station comprising a first mold section disposed on the first side plate and a second mold section disposed on the second side plate, the first mold section and the second mold section defining one or more molding cavities, the first mold section comprising a first gate adapted to inject a first molding material into each molding cavity from a first melt stream, and the second mold section comprising a second gate adapted to inject a second molding material into each molding cavity from a second melt stream; and an indexing plate assembly rotatably attached to the second side plate, the indexing plate assembly comprising a plurality of mold dies, each mold die operatively alignable with the molding cavity via rotation of the indexing plate assembly.

Clause 12. The rotary injection molding apparatus of clause 11, further comprising a cooling station defining a cooling chamber operatively alignable with each mold die of the indexing plate assembly via rotation of the indexing plate assembly.

Clause 13. The rotary injection molding apparatus of any of clauses 11 to 12, wherein the cooling chamber comprises at least one fluid port adapted for circulating a cooling fluid into the cooling chamber.

Clause 14. The rotary injection molding apparatus of any of clauses 11 to 13, further comprising:

an ejector station comprising an ejector cradle slidably connected to the second side plate, the ejector cradle adapted to disengage a completed plastic part from a corresponding mold die.

Clause 15. The rotary injection molding apparatus of any of clauses 11 to 14, wherein at least one of the first mold section and the second mold section comprises one or more vacuum ports, and wherein at least one of the first mold section and the second mold section comprises a groove configured to receive a vacuum venting seal.

Clause 16. A method of producing a plastic part via injection molding in a rotary injection molding apparatus, the method comprising the steps of:

aligning a mold die in a molding cavity, the molding cavity defined by a first mold section and a second mold section, each mold section comprising a gate adapted to control the flow of a molding material into the molding cavity, the gate of the first mold section located diametrically opposite the gate of the second mold section within the molding cavity;

supplying a first melt stream of molding material to the gate of the first mold section, and supplying a second melt stream of molding material to the gate of the second mold section; and opening the gates of the first mold section and the second mold section to permit molding material from the first melt stream and the second melt stream to fill the molding cavity surrounding the mold die, wherein the molding material takes the shape of the molding cavity forming a plastic part.

Clause 17. The method of clause 16, further comprising the step of realigning the mold die in a cooling chamber, wherein a cooling fluid is circulated about the cooling chamber to cool the plastic part.

Clause 18. The method of clause 16 or 17, further comprising the step of realigning the mold die in an ejector station, wherein the plastic part is removed from the mold die.

Clause 19. The method of any of clauses 16 to 18, wherein the first molding material is comprised of the same material as the second molding material.

Clause 20. The method of any of clauses 16 to 18, wherein the first molding material is comprised of a different material than the second molding material.

Clause 21. A syringe produced using the method of any of clauses 18 to 20.

Clause 22. A syringe comprising:
a barrel having a proximal end, a distal end, and a sidewall extending substantially circumferentially between the proximal end and the distal end along a longitudinal axis; and
at least two parting lines formed on the barrel substantially parallel to the longitudinal axis, the at least two parting lines corresponding to the an interface of the first mold section and the second mold section.

Clause 23. The syringe of clause 22, further comprising one or more gate marks formed on the barrel at the location of each of the gates of the first mold section and the second mold section.

Clause 24. The syringe of any of clauses 22 to 23, wherein the one or more gate marks are located on the barrel substantially perpendicular to the at least two parting lines about the longitudinal axis.

Clause 25. The syringe of any of clauses 22 to 24, further comprising a plunger inserted in the barrel and comprising at least two legs configured to engage a piston element of a fluid injector, and
wherein the plunger is inserted into the barrel such that the at least two parting lines are aligned to bisect the at least two legs to provide a visual indication of the orientation of the at least two legs.

Clause 26. The syringe of any of clauses 22 to 25, wherein at least one of the first mold section and the second mold section comprises one or more vacuum ports.

Clause 27. The syringe of any of clauses 22 to 26, wherein at least one of the first mold section and the second mold section comprises a groove configured to receive a vacuum venting seal.

These and other features and characteristics of syringes, rotary injection molding apparatuses, as well as the methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only.

DETAILED DESCRIPTION OF THE DISCLOSURE

Figure 1A:
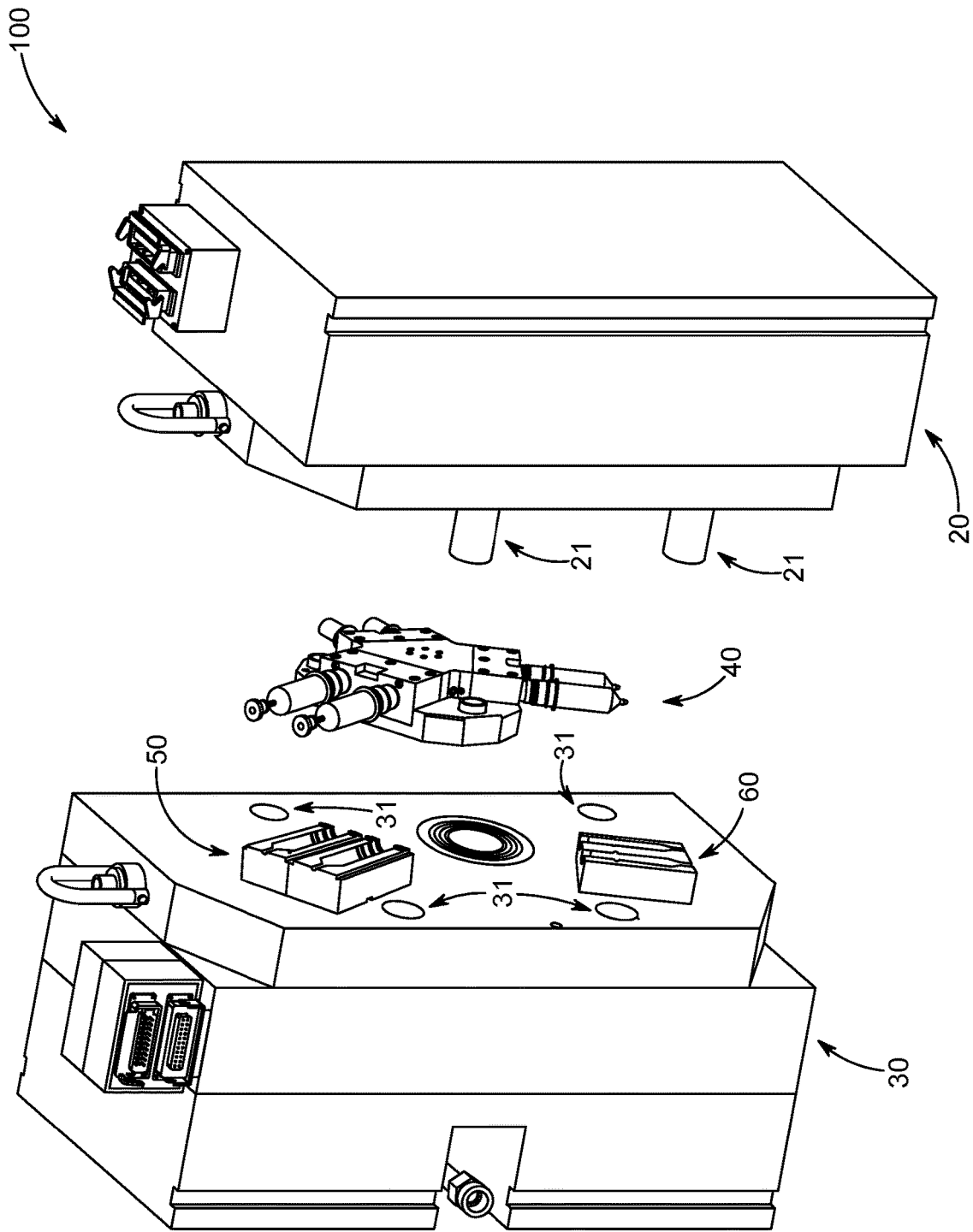
FIG. 1A is an exploded perspective view of a rotary injection molding apparatus in accordance with one example of the present disclosure, with the rotary injection molding apparatus shown in an open state or configuration.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "substantially perpendicular" means "perpendicular plus or minus 5 degrees".

The term "substantially parallel" means "parallel plus or minus 5 degrees".

The term "includes" is synonymous with "comprises".

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends.

It is to be understood that the disclosure may assume alternative variations and step sequences, except where expressly specified to the contrary. It is also to be understood that the specific devices and processes illustrated in the attached drawings, and described in the following specification, are simply examples of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to a rotary injection molding apparatus, a method of use thereof, and a plastic part produced therefrom.

Figure 1B:
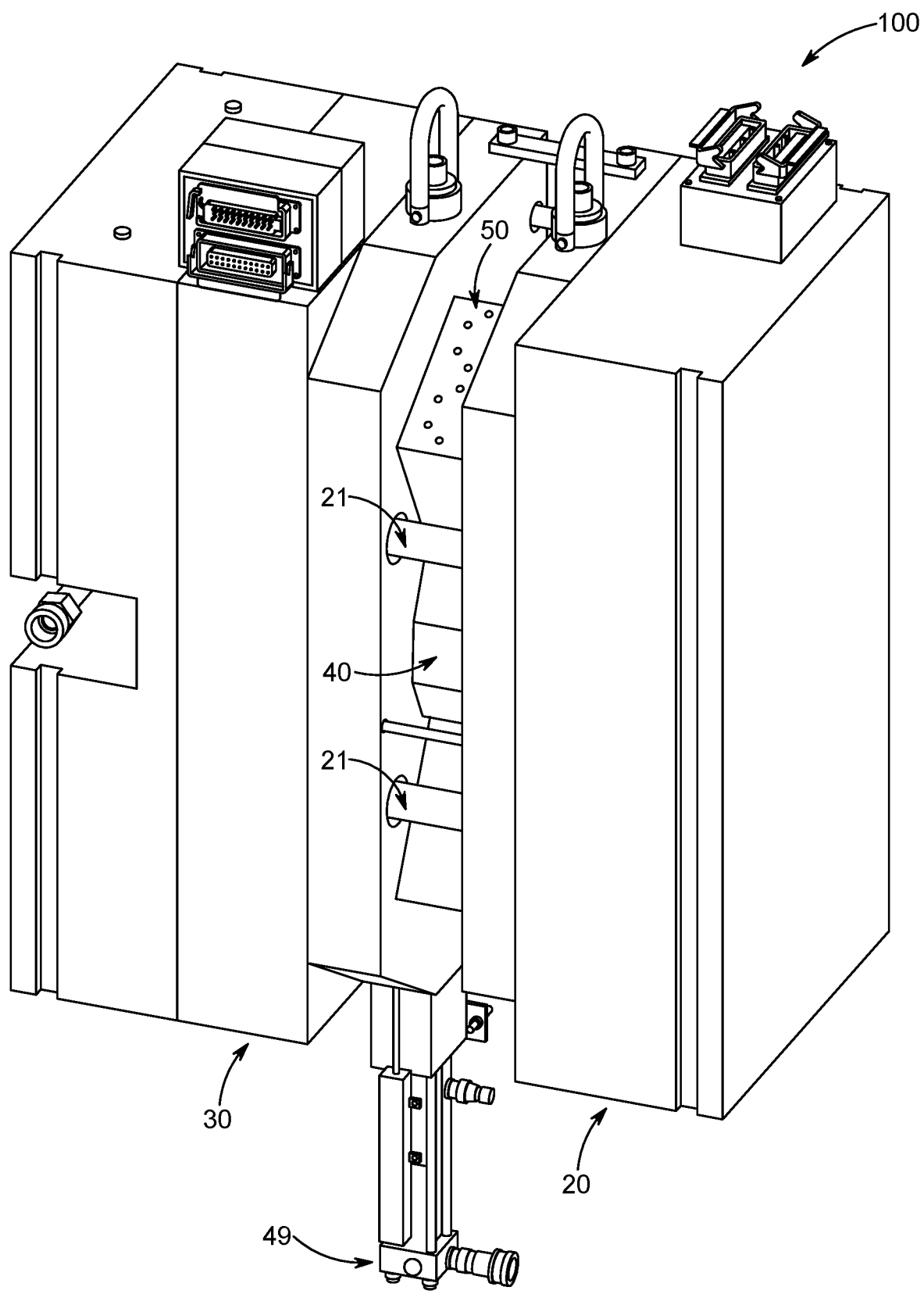
FIG. 1B is a front perspective view of the rotary injection molding apparatus of FIG. 1A shown in a closed state or configuration.

Referring now to FIGS. 1A-1B, a rotary injection molding apparatus 100 is shown. The injection molding apparatus 100 includes a stationary, first or "A" side plate 20, a slidable, second or "B" side plate 30, and a rotary indexing plate assembly 40. The apparatus is generally divided into three stations—an injection station 50, a cooling station 60, and an ejector station 70 (not shown in FIG. 1A for clarity)—which are operated in sequence to produce injection molded plastic parts. The injection station 50 and cooling station 60 each includes an "A" section and a "B" section which are disposed on the "A" side plate 20 and "B" side plate 30, respectively.

Figure 2:
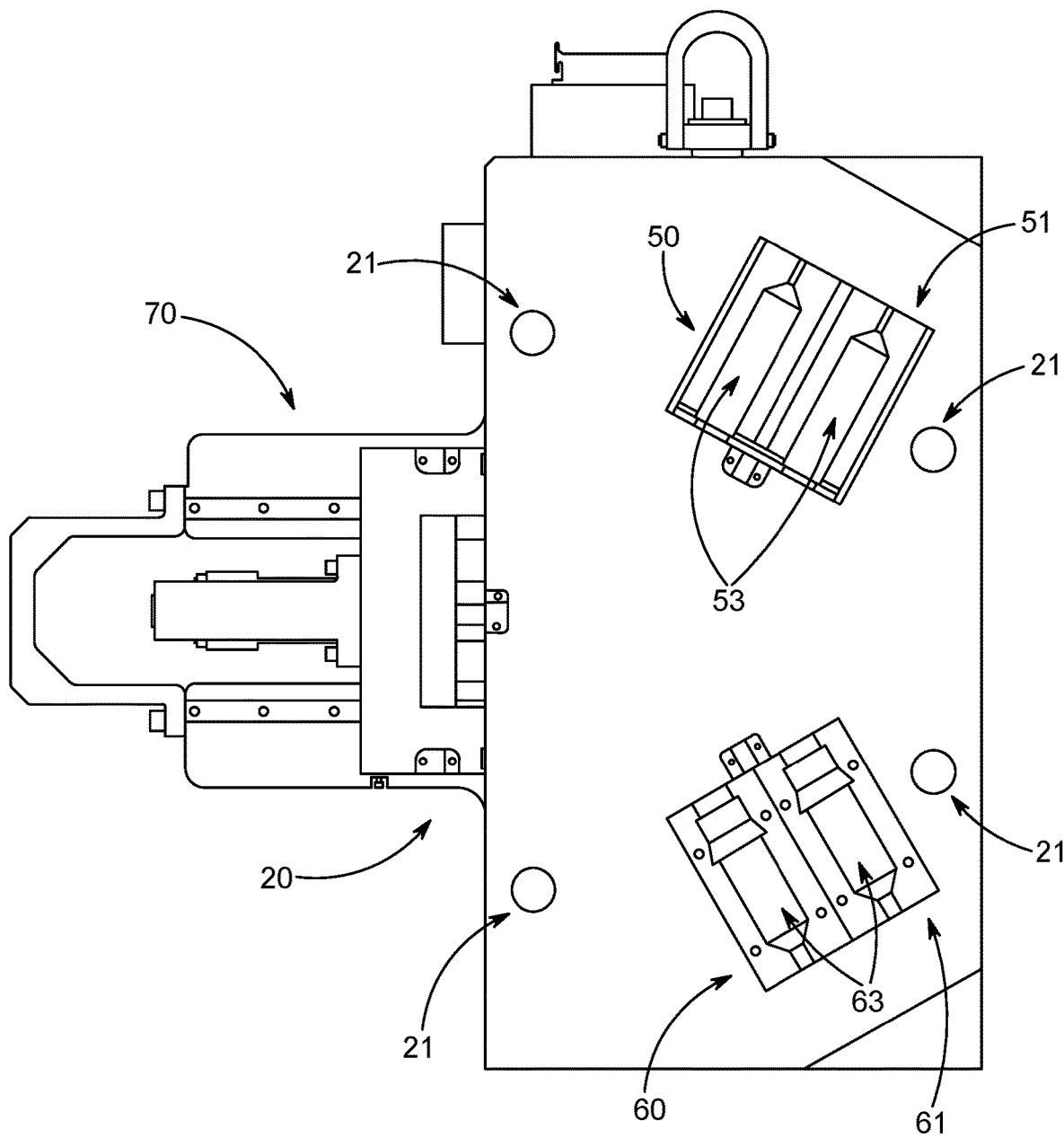
FIG. 2 is a side view of an "A" side plate of the rotary injection molding apparatus of FIG. 1A.
Figure 3:
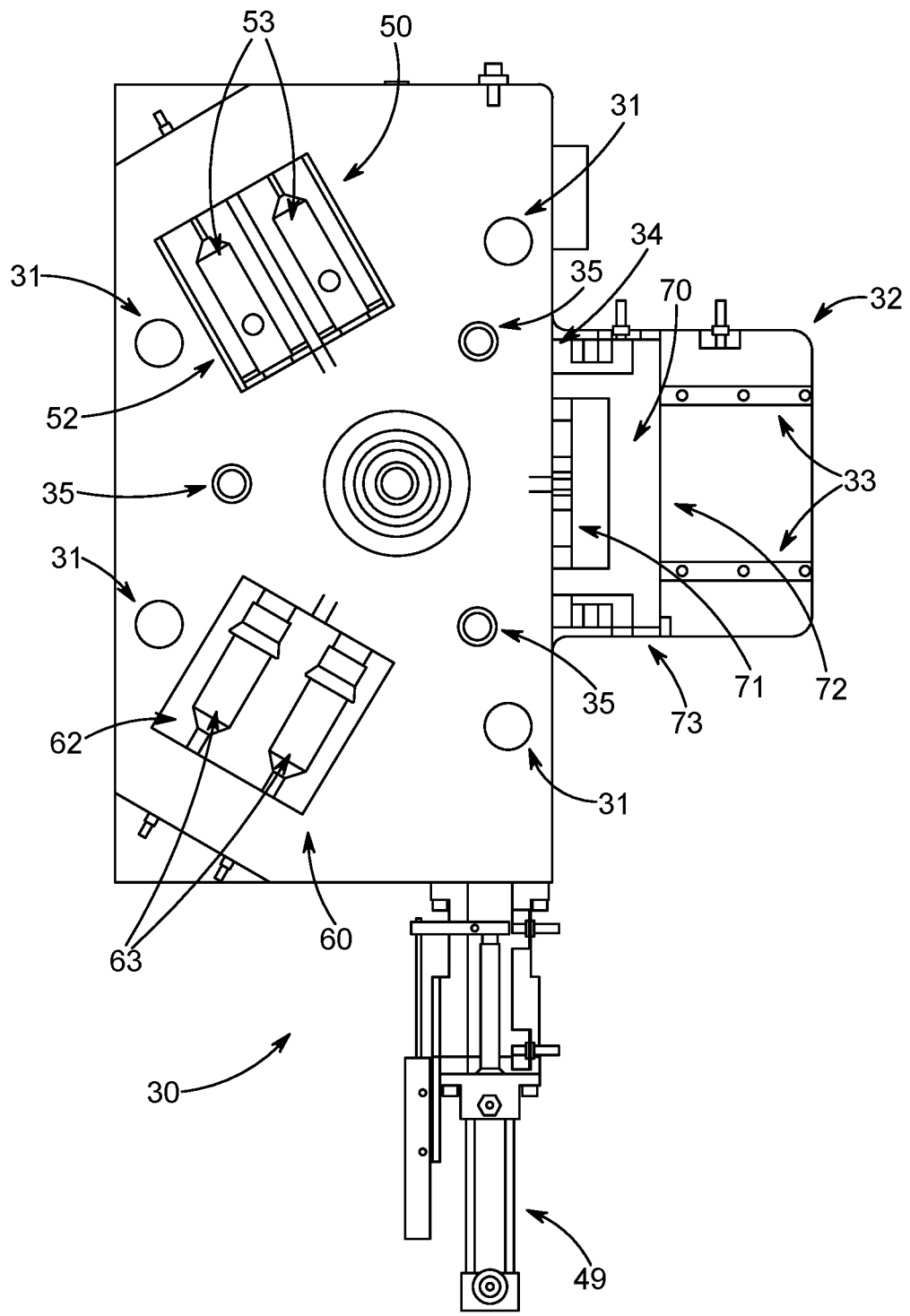
FIG. 3 is a side view of a "B" side plate of the rotary injection molding apparatus of FIG. 1A.

Referring now to FIG. 2 and FIG. 3, the stationary "A" side plate 20 includes alignment pins 21 which cooperate with alignment bores 31 in the "B" side plate 30 such that the "B" side plate 30 may slide relative to the "A" side plate 20 in a direction parallel to an axis of rotation of the indexing plate assembly 40. The slidable configuration permits the "A" side plate 20 and the "B" side plate 30 to be brought together or moved apart from each other. Sliding the "B" side plate 30 relative to the "A" side plate 20 in this manner opens and closes the injection station 50 and the cooling station 60 to permit the rotation of the indexing plate assembly 40.

Figure 4:
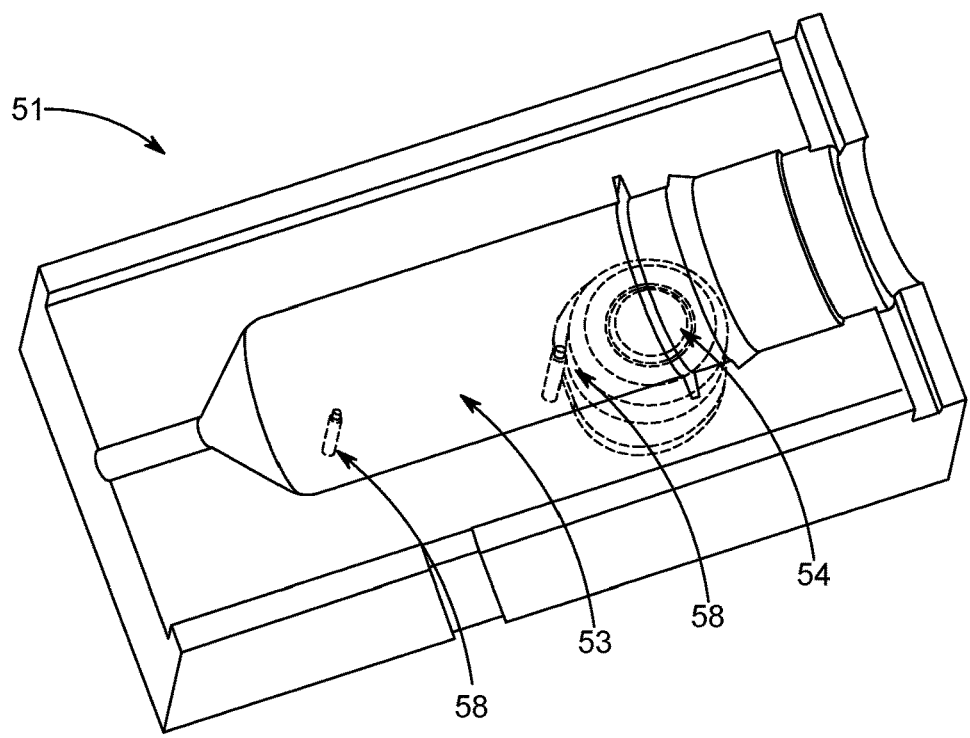
FIG. 4 is a perspective view of an "A" mold section of the "A" side plate of FIG. 2.
Figure 5:
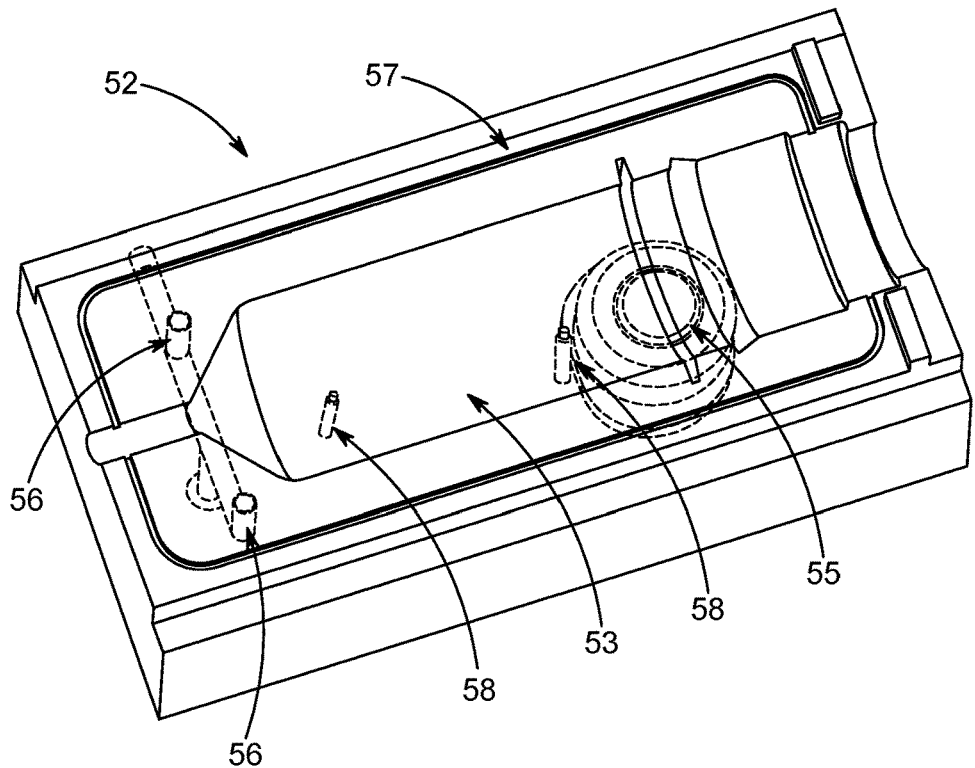
FIG. 5 is a perspective view of a "B" mold section of the "B" side plate of FIG. 3.

Referring now to FIG. 4 and FIG. 5, the injection station 50 includes at least one "A" mold section 51 and at least one "B" mold section 52, disposed on the "A" side plate 20 and "B" side plate 30, respectively. The at least one "A" mold section 51 and at least one "B" mold section 52 align to define one or more molding cavities 53. Each molding cavity 53 facilitates the production of one plastic part per molding cavity 53 per cycle. A "cycle" as used herein refers to the process beginning with injecting a molding material into the injection station 50 with the indexing plate assembly 40 in a first position, and ending with rotating the indexing plate assembly 40 back to the first position after a plastic part has been ejected.

The example shown in FIG. 3 includes two molding cavities 53; thus, the example shown is capable of producing two plastic parts per cycle. Each molding cavity 53 includes an "A" gate 54, located in the "A" mold section 51, and a "B" gate 55, located in the "B" mold section 52, through which liquid molding material is injected into the molding cavity 53. In this configuration, molding material may be injected through the "A" and "B" gates 54, 55, such that the molding cavity 53 is filled from diametrically opposite sides. In some examples, opening the "A" and "B" gates 54, 55 to inject the molding material may be performed simultaneously. Thus, filling of each side of the molding cavity 53 is distributed approximately evenly between the "A" and "B" gates 54, 55. In other examples, the opening of one of the "A" gate 54 or the "B" gate 55 may be delayed with respect to the other in order to calibrate the gates 54, 55 with one another or to inject molding material from the gates 54, 55 at different times or rates. The liquid molding material may be a polymer resin, molten metal, or other suitable material which is capable of being cooled to form a solid part. The following description generally refers to parts made of plastic, but it is to be understood that such parts could also be made from metal, glass, or other suitable materials depending on the molding material used.

Molding material is supplied to each "A" mold section 51 and each "B" mold section 52 from independent melt streams, with a first melt stream supplying molding material to the "A" gate 54 of each molding cavity 53, and a second melt stream supplying molding material to the "B" gate 55 of each molding cavity 53. Each melt stream may be generated by, for example, an injection molding screw (not shown). The molding material in the first melt stream and the molding material in the second melt stream may be either the same or different materials, and may each be selected, for example, from a list of thermoplastic materials, thermoset materials, liquid metals, and other suitable materials.

In one example of the present disclosure, the "B" mold section 52 includes one or more vacuum ports 56 through which the molding cavities 53 can be vented to relieve pressure accumulated during the injection molding process. A vacuum venting seal is disposed in a groove 57 in the "B" mold section 52.

In another example, each molding cavity 53 further includes one or more sensors 58 adapted to monitor the pressure, temperature, and/or other properties of the molding material in the molding cavity 53 during the mold process.

Figure 6:
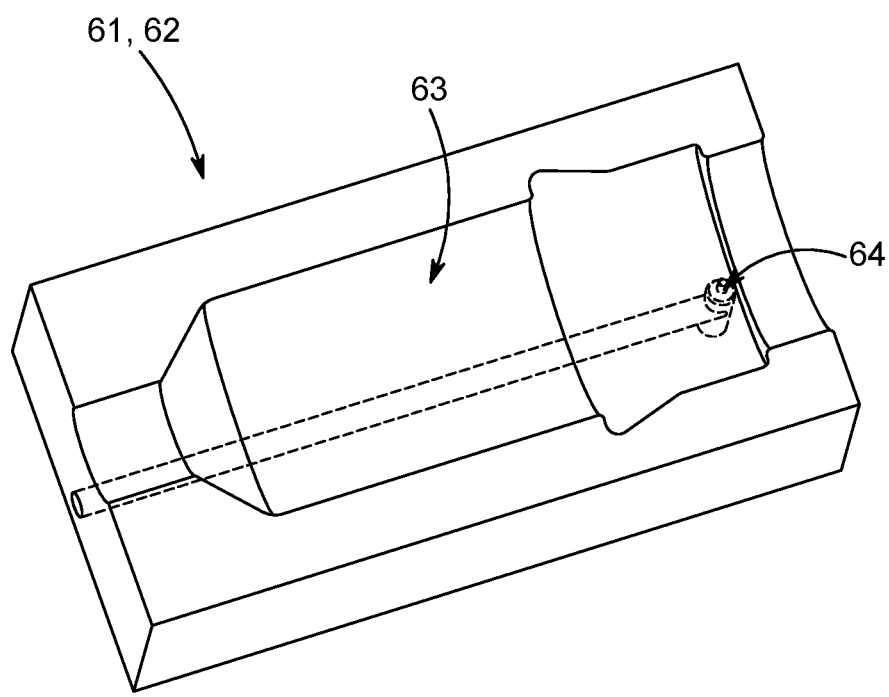
FIG. 6 is a perspective view of a cooling section of the "A" side plate and "B" side plate of FIG. 2 and FIG. 3, respectively.

Referring now to FIG. 6, the cooling station 60 includes at least one "A" cooling section 61 and at least one "B" cooling section 62, disposed on the "A" side plate 20 and "B" side plate 30, respectively. The "A" cooling section 61 and the "B" cooling section 62 are substantially identical. The "A" cooling section 61 and the "B" cooling section 62 align to define a number of cooling chambers 63 equal to the number of molding cavities 53 in the injection station 50. Each cooling chamber 63 is oversized relative to each molding cavity 53 such that when the plastic part is positioned in the cooling chamber 63, a cooling fluid such as a cooling liquid or a cooling gas, such as air, may flow around an outer surface of the plastic part. Each cooling chamber 63 includes a fluid port 64 in the "A" cooling section 61 and a fluid port 64 in the "B" cooling section 62 through which the cooling fluid is injected and circulated around the part in the cooling chamber 63. Each cooling chamber 63 may further include an additional port through which cooling fluid is injected and circulated against an inner surface of the part to provide additional heat dissipation.

Now referring back to FIG. 3, the ejector station 70 includes an ejector cradle 71 shaped for receiving completed plastic parts and translating the parts off of the indexing plate assembly 40. The "B" side plate 30 is provided with an extension 32 having a pair of guide bars 33 and end stops (not shown) secured thereon. The ejector cradle 71 is carried by an ejector plate 72, which is movably mounted relative to the "B" side plate 30 such that the ejector plate 72 may slide back and forth along the guide bars 33 between an edge 34 of the "B" side plate 30 (starting position) and the end stops (finishing position). A limit switch 73 is mounted on the extension 32 and is used to restore the ejector plate 72 to its starting position. The example in FIG. 3 is shown in the starting position.

Figure 7:
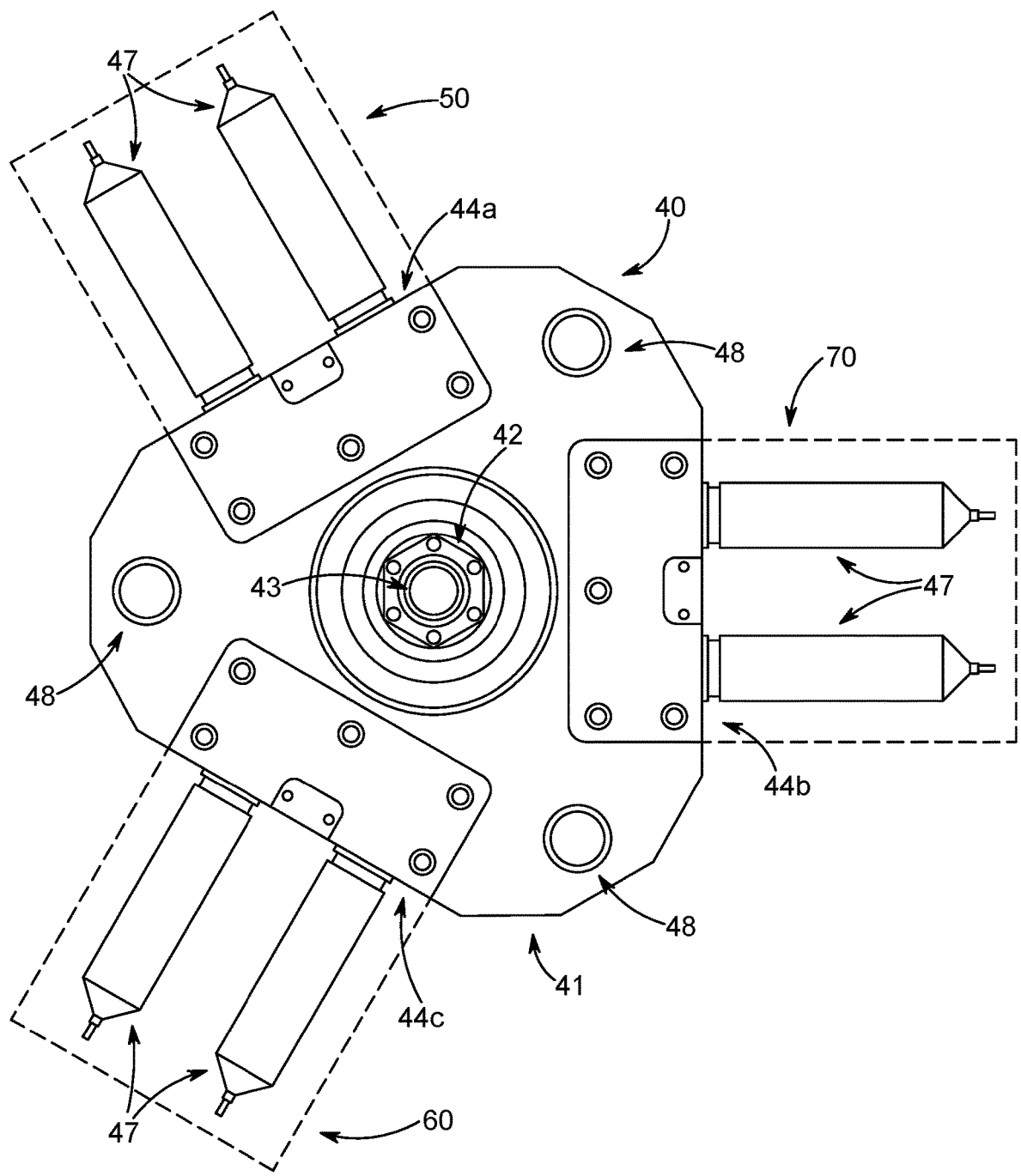
FIG. 7 is a side view of a indexing plate assembly of the rotary injection molding apparatus of FIG. 1.

Referring now to FIG. 7, according to one example of the disclosure, the indexing plate assembly 40 has a generally triangular base 41 affixed to a center hub 42 and rotating shaft 43. The indexing plate assembly 40 includes three mold dies 44a, 44b, 44c arranged concentrically about the axis of rotation in 120° increments, each mold die having a number of cores 47 equal to the number of molding cavities 53 in the injection station 50. In other examples, the indexing plate assembly 40 may include any number of mold dies 44, for example, two, arranged about the axis of rotation in increments of, for example, 180°.

Rotation of the shaft 43 is controlled by mechanical means such as, but not limited to, an electric servo motor or hydraulic cylinder 49 (See FIG. 1). For example, the shaft 43 may carry a pinion gear which is engageable with a toothed rack attached to a piston rod of a hydraulic cylinder 49 as shown in FIG. 1. Extension and retraction of the piston rod of cylinder 49 causes the indexing plate assembly 40 to rotate in 120° increments, such that the mold dies 44a, 44b, 44c are operatively aligned with the injection station 50, the cooling station 60, and the ejector station 70. The injection station 50, the cooling station 60, and the ejector station 70 are shown generally in broken lines in FIG. 7 to illustrate their respective positions relative to the indexing plate assembly 40 according to an example of the invention.

The indexing plate assembly 40 includes a series of guide bushings 48 spaced concentrically about the axis of rotation of the indexing plate assembly 40. The guide bushings 48 align with dowel pins 35 on the "B" side plate 30 (see FIG. 3) to maintain rigid operative alignment between the mold dies 44a, 44b, 44c and the injection station 50, cooling station 60, and ejector station 70. The dowel pins 35 are arranged concentrically about the axis of rotation of the indexing plate assembly 40, such that the guide bushings 48 may engage the dowel pins 35 in three orientations corresponding to 120° increments of rotation of the indexing plate assembly 40. In order for the indexing plate assembly 40 to be rotated, the indexing plate assembly 40 is extended away from the "B" side plate 30 until the guide bushings 48 clear the dowel pins 35. Then, the indexing plate assembly 40 is rotated to the desired position, and retracted back towards the "B" side plate 30, such that the guide bushings 48 slide over the dowel pins 35 in a new orientation relative to the "B" side plate 30.

Operation of the apparatus described herein to produce plastic parts is achieved as follows. Molding material from multiple melt streams is injected into each molding cavity 53 of the injection station 50 through the "A" and "B" gates 54, 55. The "B" side plate 30 is then slid away from the "A" side plate 20 along the alignment pins 21, thereby opening the injection station 50 and cooling station 60. The indexing plate assembly 40 is extended away from the "B" side plate 30 such that the triangular base 41 clears the dowel pins 35, and the indexing plate assembly 40 is rotated forwardly 120°. The direction of rotation is such that the mold dies are positioned in sequence from the injection station 50, to the cooling station 60, to the ejector station 70, and back to the injection station 50. The indexing plate is then retracted onto the "B" side plate 30, such that the guide bushings 48 align with the dowel pins 35 in the desired orientation. The "B" side plate 30 is then retracted back toward the "A" side plate 20, closing the injection station 50 and cooling station 60. Molding material is again injected into the molding cavities 53 around the mold dies 44a, 44b, 44c which were previously indexed in the ejector station 70. Concurrently, cooling fluid is circulated into the cooling station 60 to cool the plastic parts previously formed in the injection station 50. Also concurrently, the plastic parts previously in the cooling station 60 are removed from the mold dies 44a, 44b, 44c at the ejector station 70. The apparatus thus permits, though is not limited to, simultaneous injection, cooling, and ejection of plastic parts.

Each step of the indexing process takes approximately 1 to 30 seconds, resulting in an overall cycle time of approximately 5 to 40 seconds from injecting the molding material to ejecting the completed plastic part. The overall cycle time may be, for example, 20 seconds. Depending on the type of molding material used and the design of the part to be produced, the injection step may take, for example, 14 seconds from insertion of molding material into the injection station 50 until the part is rotated into the cooling station 60. This includes both the time to inject the molding material into the injector station 50 and a preliminary cooling phase which may be required before the part can be removed from the mold sections 51, 52.

Figure 8:
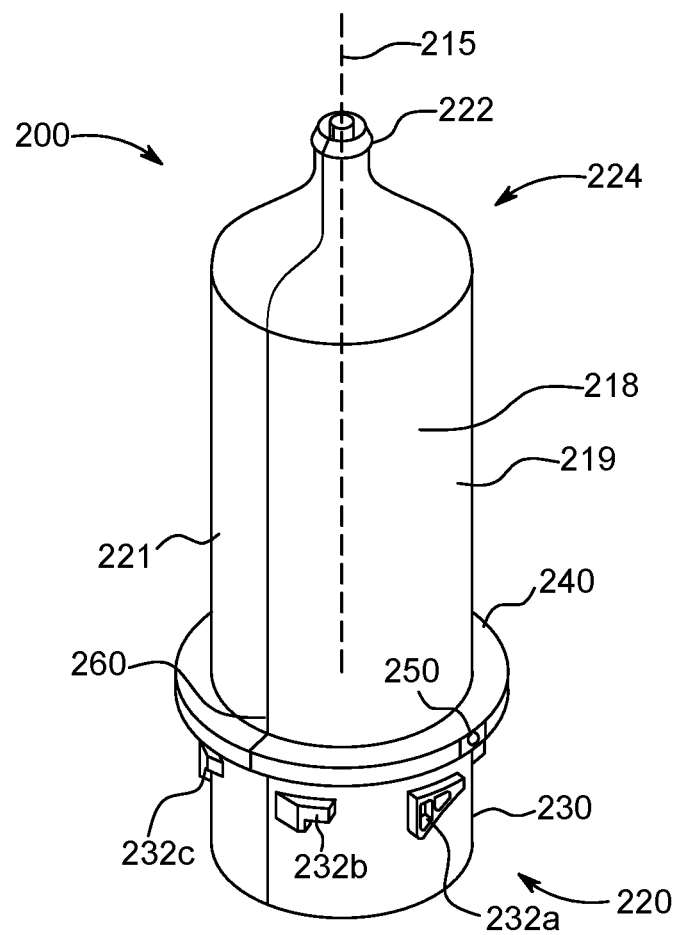
FIG. 8 is a perspective view of an exemplary syringe produced by the rotary injection molding apparatus of FIG. 1A.
Figure 9:
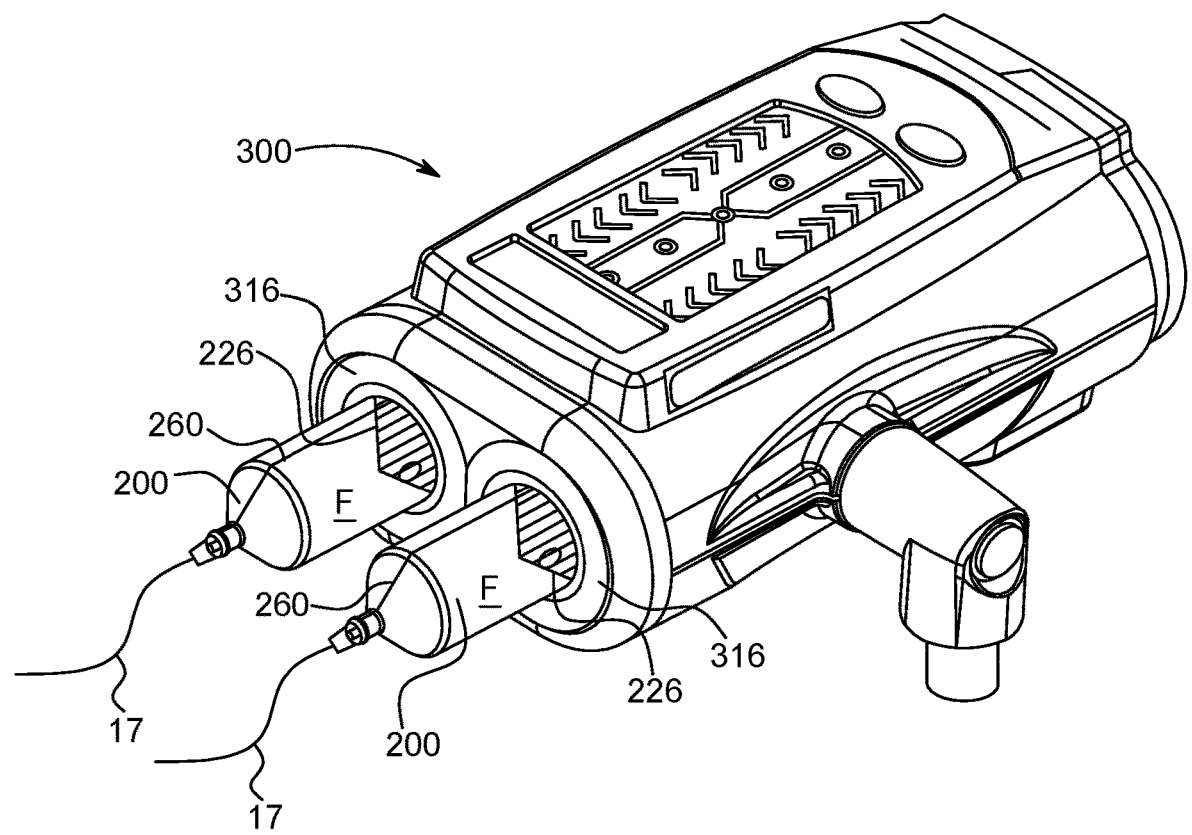
FIG. 9 is a perspective view of a fluid injector adapted to accept the syringe of FIG. 8.

Referring now to FIG. 8, the present disclosure also relates to a syringe 200 for medical use. In some examples, the syringe 200 may be produced using the injection molding apparatus 100 and methods for using the injection molding apparatus 100 described herein. The syringe 200 may be configured for use in a fluid injector 300 (hereinafter referred to as "injector 300"), such as an automated or powered fluid injector, as shown in FIG. 9. The injector 300 is adapted to interface with and actuate one or more syringes 200, which may be filed with a fluid F, such as contrast media, saline solution, or any desired medical fluid. The injector 300 may be used during a medical procedure to inject the medical fluid into the body of a patient by driving a plunger 226 of the syringe 200 with a linear actuator or a piston element 320. The plunger 226 may include one or more flexible legs 228 configured to engage the linear actuator or piston element 320.

As will be described hereinafter, in some examples, the syringe 200 includes one or more syringe retaining members 232 configured for retaining the syringe 200 within a syringe port 316 of the injector 300. The one or more syringe retaining members 232 is configured to operatively engage a locking mechanism of the injector 300 to facilitate loading or removal of the syringe 200 to and from the injector 300. A fluid path set 17 may be fluidly connected with the syringe 200 for delivering the fluid F from the syringe 200 to a catheter (not shown) inserted into a patient at a vascular access site.

The syringe 200 generally has a cylindrical syringe barrel 218 formed from glass, metal, or a suitable medical-grade plastic. The barrel 218 has a proximal end 220 and a distal end 224, with a sidewall 219 extending therebetween along a length of a longitudinal axis 215 extending through a center of the barrel 218. In some examples, the distal end 224 may have a conical shape that narrows in a distal direction from the cylindrical barrel 218. A nozzle 222 extends from the distal end 224. The barrel 218 has an outer surface 221 and an inner surface that defines an interior volume configured for receiving the fluid F therein. The proximal end 220 of the barrel 218 may be sealed with the plunger 226 that is slidable through the barrel 218.

With continued reference to FIG. 8, the proximal end 220 of the syringe 200 is sized and adapted for being removably inserted in the syringe port 316 of the injector 300 (see FIG. 9). In some examples, the proximal end 220 of the syringe 200 defines an insertion section 230 that is configured to be removably inserted into the syringe port 316 of the injector 300 while the remaining portion of the syringe 200 remains outside of the syringe port 316. As described in detail herein, in certain examples, the proximal end 220 of the syringe 200 includes one or more syringe retaining members 232 adapted to form a locking engagement with a corresponding locking mechanism in the syringe port 316 of the injector 10 for retaining the syringe 200 in the syringe port 316. The combination of the syringe 200 having the one or more syringe retaining members 232 and the locking mechanism of the injector 300 defines a connection interface for loading and unloading of the syringe 200 to and from the injector 10. In some examples, the one or more syringe retaining members 232 cooperate with at least a portion of the locking mechanism to self-orient the syringe 200 relative to the syringe port 316 such that the syringe 200 may be releasably locked with the syringe port 316.

The one or more syringe retaining members 232 may be formed integrally on the outer surface 221 of the insertion section 230 of the barrel 218. The one or more syringe retaining members 232 may be identical to or different from one another. In the example shown in FIG. 8, the syringe 200 may have two sets of three different syringe retaining members 232. For example, the syringe 200 may have a pair of first syringe retaining members 232a positioned diametrically opposite to one another, a pair of second syringe retaining members 232b circumferentially offset relative to the pair of first syringe retaining members 232a in a first direction, and a pair of third syringe retaining members 232c circumferentially offset relative to the pair of first syringe retaining members in a second direction. The first, second, and third syringe retaining members 232a, 232b, 232c are collectively referred to as "syringe retaining members 232". With this arrangement, each first syringe retaining member 232a is surrounded by the second syringe retaining member 232b on one side thereof and the third syringe retaining member 232c on the other side thereof. One of ordinary skill in the art will appreciate that other arrangements of one or more sets of same or different syringe retaining members 232 can be easily conceived.

Figure 10:
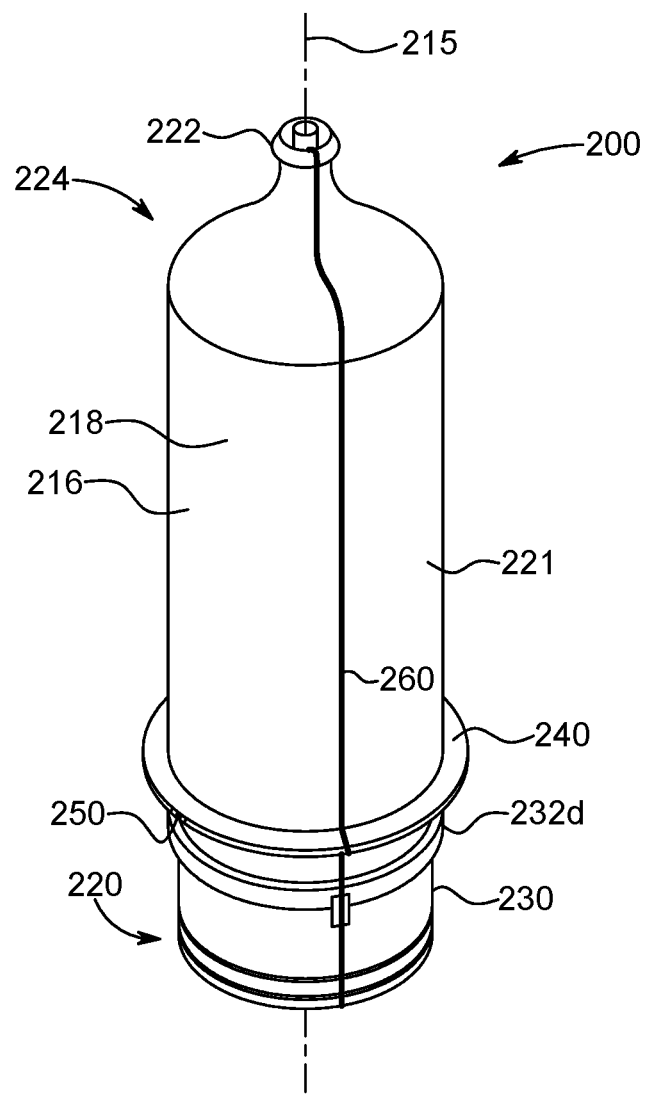
FIG. 10 is a perspective view of another example of a syringe produced by the rotary injection molding apparatus of FIG. 1.

In other examples, the one or more syringe retaining members 232 may include a retaining flange 232d encircling at least a portion of the insertion portion 230 as shown in FIG. 10. The retaining flange 232d may have a triangular profile corresponding to the syringe port 316 of the injector 300.

In some examples, the syringe 200 may include a drip flange 240 encircling at least a portion of the barrel 218 distally located relative to the insertion section 230. The drip flange 240 provides a physical obstruction to protect the injector 300 from fluid F dripping or running down from the nozzle 222.

The structural features of the syringe 200, including but not limited to the barrel 218, the nozzle 222, the one or more retaining members 232, and the drip flange 240 may be formed integrally with the syringe 200 using the injection molding apparatus 100 by configuring each molding cavity 53 of injection station 50 to correspond with the desired shape and profile of the structural features of the syringe 200. That is, each external feature of the syringe 200 may correspond to a relief in the molding cavity 53, such that the molding material entering the mold cavity solidifies in the desired shape of the syringe 200.

The syringe 200 may include at least two parting lines 260 on diametrically opposed sides of the barrel 218 corresponding to the interface of the "A" mold section 51 and the "B" mold section 52. The at least two parting lines 260 may also correspond to a meeting line of the first melt stream injected from the "A" gate 54 and the second melt stream injected from the "B" gate 55. The syringe 200 may include one or more gate marks 250 corresponding to the location of the gates 54, 55. For example, each of the "A" and "B" gates 54, 55 of the injection station 50 may leave a gate mark 250 on the syringe 200 at the location of the gates 54, 55 as a byproduct of the injection process. Each gate mark 250 may include an imprint corresponding to the shape of the gate 54, 55.

Figure 12:
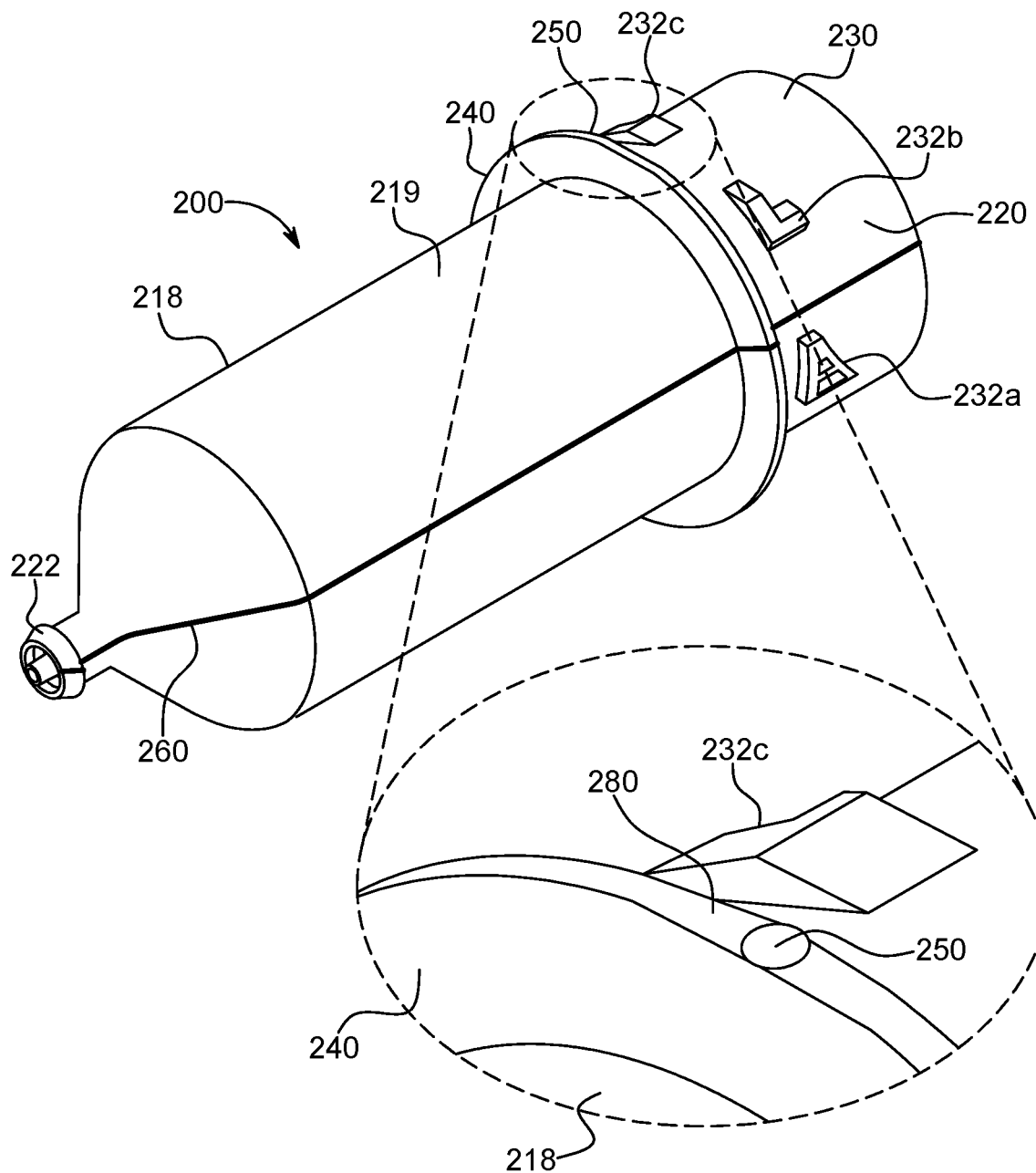
FIG. 12 is a perspective and detail view of a gate mark of another example of a syringe produced by the rotary injection molding apparatus of FIG. 1.
Figure 13:
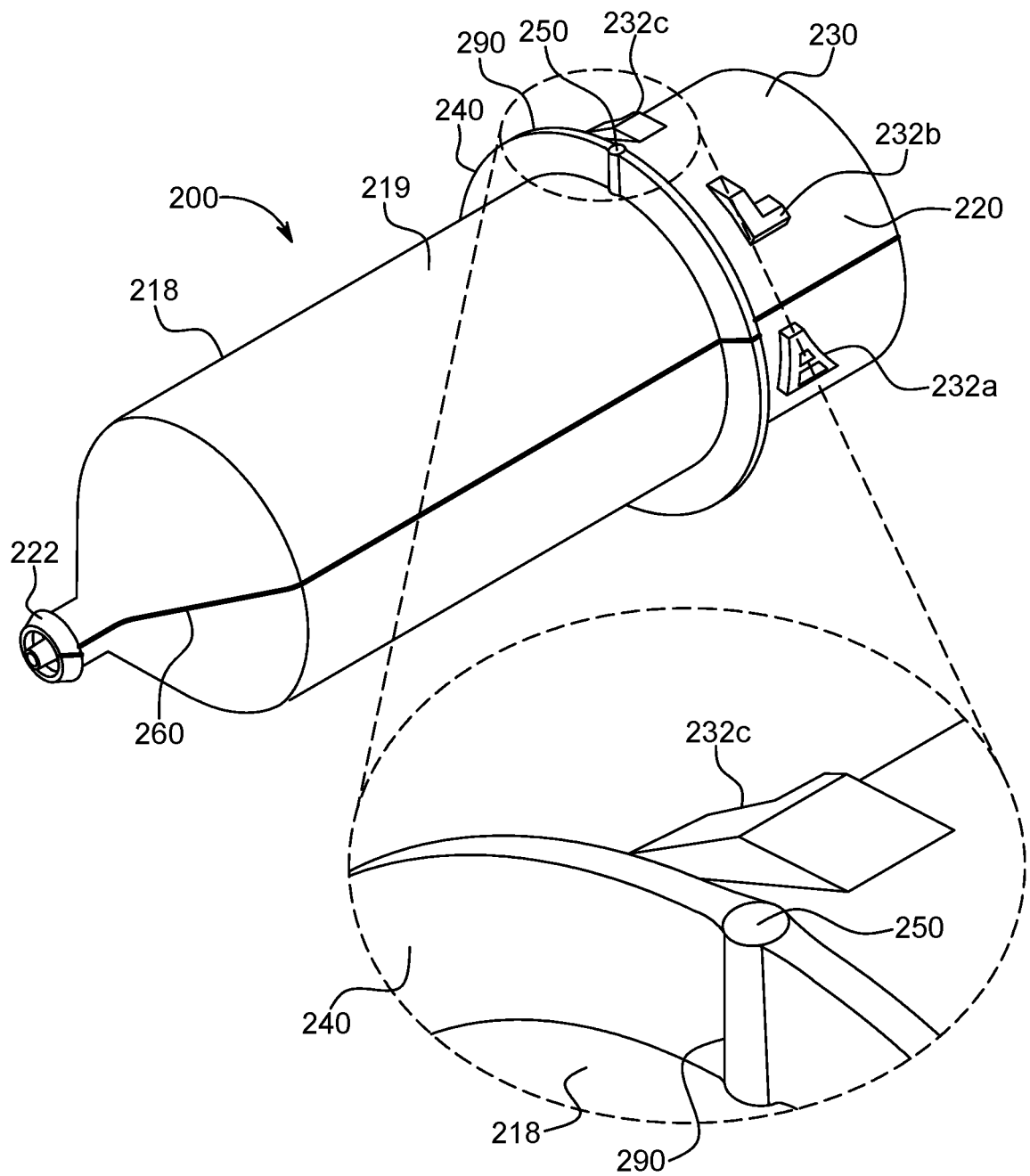
FIG. 13 is a perspective and detail view of a gate mark of another example of a syringe produced by the rotary injection molding apparatus of FIG. 1.

As may be appreciated from FIGS. 8, 10, 12, and 13, in some examples, one or more gate marks 250 may be located on edges of the drip flange 240 of the syringe 200 corresponding to the location of each of the "A" and "B" gates 54, 55 of the injection station 50. Locating the gates 54, 55 on the edge of the drip flange 240 or another surface of the barrel 218 that is not in contact with the fluid F ensures that any discoloration or haziness left at the gate marks 250 as a result of the injection process does not obstruct visibility into the barrel of the syringe 200. Referring to FIG. 12, the drip flange 240 may include one or more flat sections 280 on an outside perimeter surface of the drip flange 240 corresponding to the locations of the gates 54, 55, and on which the gate marks 250 are formed. Referring to FIG. 13, the drip flange 240 may include one or more injection protrusions 290 corresponding to the locations of the gates 54, 55, and on which the gate marks 250 are formed. The one or more injection protrusions 290 may extend radially from the edge of the drip flange 240 to the sidewall 219 of the barrel 218 along at least one of a top surface and a bottom surface of the drip flange 240. The one or more injection protrusions 290 provide additional material thickness at the location of the gates 54, 55 to ensure that the molding material injected from the gates 54, 55 has a sufficiently large flow path to the barrel 218. The gate marks 250 may be located substantially perpendicular to the parting lines 260 about the longitudinal axis 215 to ensure that the molding material injected from the "A" gate 54 and the "B" gate 55 meet or converge substantially at the parting lines 260 parallel to the longitudinal axis 215 of the barrel 218.

Figure 11:
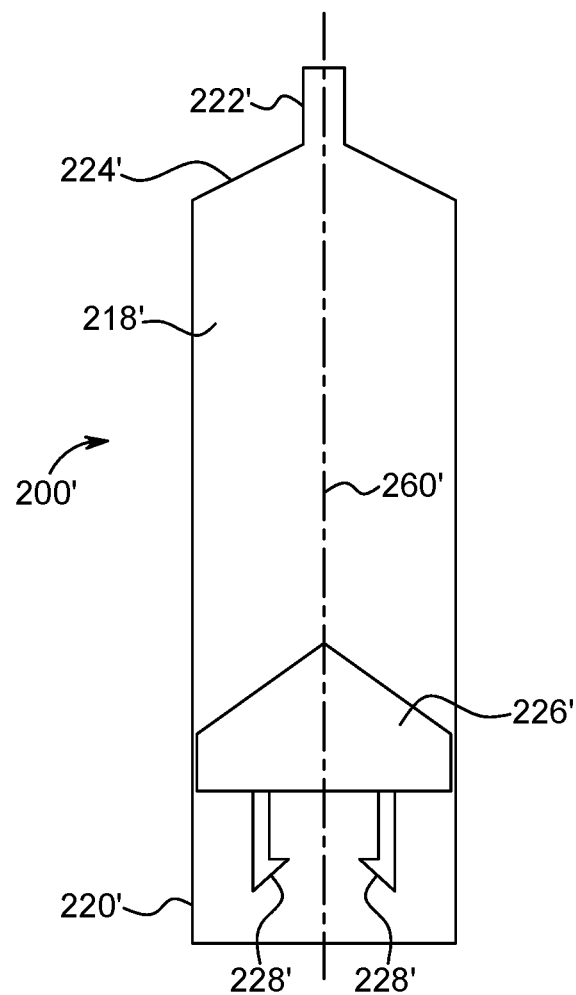
FIG. 11 is a side schematic view of another example of a syringe produced by the rotary injection molding apparatus of FIG. 1, with a plunger inserted into the barrel.

One or more of the gate mark 250 and/or one or more of the parting lines 260 may be configured for use in aligning the syringe 200 with the plunger 226. In some examples, as shown in FIG. 11, the plunger 226 may be inserted into the syringe 200 such that one or more of the parting lines 260 bisects two of the plunger legs 228. This configuration provides a user with visual verification that the syringe 200 and the plunger 226 are in proper operative alignment for performing an injection of the fluid F. For example, upon the forming of the syringe 200, the plunger 226 may be inserted into the syringe barrel 218 in such a manner that the at least two parting lines 260 are aligned such that a plane passing through the at least two parting lines 260 passes between and, ideally, bisects the two plunger legs 228, which are configured to engage a piston element extendable and retractable by the fluid injector 300. As such, a user of the fluid injector 300 who is handling the syringe 200 is provided with a visual indication of the orientation of the plunger legs 228 and this visual indicator can be used as a visual prompt for the user to assist the user in loading the syringe 200 into engagement with the fluid injector 300 so that the plunger legs 228 are properly oriented to be engaged and captured by the piston element of the fluid injector 300.

The syringe 200 may be adapted for use in CT, MRI, PET, and like procedures and operable at typical operating pressures of, for example, about 50 psi to 250 psi, depending on the viscosity of the fluid, type of procedure, and the desired rate of injection. The syringe 200 may also be adapted for use in CV and like procedures and operable at typical operating pressures of, for example, about 400 psi to 600 psi, depending on the viscosity of the fluid, type of procedure, and the desired rate of injection. Other exemplary syringes suitable for production using the injection molding apparatus 100 of FIG. 1 are described in U.S. Pat. Nos. 5,383,858; 6,322,535; 6,652,489; 9,173,995; and 9,199,033, the disclosures of which are all incorporated by reference in their entirety.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

What is claimed is:

1. A syringe comprising:
   a barrel having a proximal end, a distal end, and a sidewall extending substantially circumferentially between the proximal end and the distal end along a longitudinal axis;
   a drip flange extending radially outward from the barrel, the drip flange having a pair of protrusions protruding axially relative to the drip flange and extending radially from an edge of the drip flange to the sidewall along at least one of a top surface and a bottom surface of the drip flange; and
   a pair of gate marks each formed on one of the pair of protrusions on the drip flange,
   wherein the barrel is formed from an injection molding process comprising:
   aligning a mold die defining an internal shape of the barrel in a molding cavity defining an external shape of the barrel, the molding cavity defined by a first mold section and a second mold section, each mold section comprising a gate adapted to control flow of a molding material into the molding cavity, the gate of the first mold section located diametrically opposite the gate of the second mold section within the molding cavity;
   supplying a first melt stream of the molding material to the gate of the first mold section, and supplying a second melt stream of the molding material to the gate of the second mold section; and
   opening the gate of the first mold section and the gate of the second mold section to permit the molding material from the first melt stream and the second melt stream to fill the molding cavity surrounding the mold die, wherein the molding material takes a shape of the molding cavity, and
   wherein a first of the pair of gate marks is formed on the drip flange at a location of the gate of the first mold section and a second of the pair of gate marks is formed on the drip flange at the location of the gate of the second mold section.

2. The syringe of claim 1, further comprising parting lines formed on the barrel substantially parallel to the longitudinal axis, the parting lines corresponding to an interface of the first mold section and the second mold section.

3. The syringe of claim 2, further comprising a plunger inserted in the barrel and comprising at least two legs configured to engage a piston element of a fluid injector, and
   wherein the plunger is inserted in the barrel such that the parting lines are aligned to bisect the at least two legs to provide a visual indication of an orientation of the at least two legs.

4. The syringe of claim 1, wherein at least one of the first mold section and the second mold section comprises one or more vacuum ports.

5. The syringe of claim 1, wherein at least one of the first mold section and the second mold section comprises a groove configured to receive a vacuum venting seal.

6. The syringe of claim 1, wherein the injection molding process is performed using a rotary injection molding apparatus.

7. The syringe of claim 6, wherein the rotary injection molding apparatus comprises:
   a stationary first side plate comprising a plurality of alignment pins protruding from the stationary first side plate;
   a second side plate slidably attached to the stationary first side plate, the second side plate comprising a plurality of alignment bores engageable with the plurality of alignment pins;
   an injection station comprising the first mold section disposed on the first side plate and the second mold section disposed on the second side plate, the first mold section and the second mold section defining the molding cavity, the first mold section comprising a first gate adapted to inject a first molding material into the molding cavity from a first melt stream, and the second mold section comprising a second gate adapted to inject a second molding material into the molding cavity from a second melt stream; and
   an indexing plate assembly rotatably attached to the second side plate, the indexing plate assembly comprising a plurality of mold dies, each mold die operatively alignable with the molding cavity via rotation of the indexing plate assembly.

8. The syringe of claim 7, wherein the rotary injection molding apparatus further comprises:
   a cooling station defining a cooling chamber operatively alignable with each mold die of the indexing plate assembly via rotation of the indexing plate assembly, wherein the cooling chamber comprises at least one fluid port adapted for circulating a cooling fluid into the cooling chamber.

\* \* \* \* \*

UNITED STATES PATENT AND TRADEMARK OFFICE
CERTIFICATE OF CORRECTION

PATENT NO. : 11,999,084 B2  
APPLICATION NO. : 16/334463  
DATED : June 4, 2024  
INVENTOR(S) : Cain et al.

Page 1 of 1

It is certified that error appears in the above-identified patent and that said Letters Patent is hereby corrected as shown below:

In the Specification

In Column 2, Line 28, delete "that" and insert -- from --, therefor.

In Column 7, Line 36, delete "the an" and insert -- an --, therefor.

In the Claims

In Column 16, Line 48, in Claim 7, delete "the first" and insert -- the stationary first --, therefor.

Signed and Sealed this
Eighteenth Day of February, 2025

Coke Morgan Stewart
*Acting Director of the United States Patent and Trademark Office*